United States Patent [19]

Gerlach

[11] Patent Number: 5,516,691
[45] Date of Patent: May 14, 1996

[54] MODULE FOR CULTURING AND USING METABOLISMS AND/OR FOR MAINTAINING MICROORGANISMS

[76] Inventor: Jörg Gerlach, Kopischstrasse 10, 10965, Berlin, Germany

[21] Appl. No.: 117,429

[22] Filed: Sep. 7, 1993

[30] Foreign Application Priority Data

Sep. 9, 1992 [DE] Germany .................. 42 30 194.7

[51] Int. Cl.⁶ .............................. C12M 3/00; C12N 5/00
[52] U.S. Cl. .................... 435/297.1; 435/240.1; 435/240.33; 435/240.242; 435/289.1; 435/297.4
[58] Field of Search ............. 435/240.1, 240.2, 435/240.21, 240.23, 240.241, 240.242, 287, 313, 316, 284

[56] References Cited

U.S. PATENT DOCUMENTS 3,734,851  5/1973  Matsumura ..................... 210/22
4,720,462  1/1988  Rosenson ....................... 435/285
5,290,366  3/1994  Riermeier et al. ............. 136/244
5,290,700  3/1991  Binot et al. .................... 435/284

OTHER PUBLICATIONS

Gerlach, et al. Artificial Organs 14(5):328–333 1990.

Primary Examiner—Michael G. Wityshyn
Assistant Examiner—Jane Williams
Attorney, Agent, or Firm—Marshall & Melhorn

[57] ABSTRACT

This invention relates to a module (1) for culturing and using metabolisms for maintaining microorganisms (9), particularly for cells or bacteria, comprising an outer casing (2), at least three independent membrane systems, whereof at least two are constructed as hollow fiber membranes (3) and are located in the inner space (4) of the module (1), and that the hollow fiber membranes (3) form a close packed, space network (5) and microorganisms (9) are located in the cavities of the network (5) and/or adhere to the hollow fiber membranes (3).

10 Claims, 8 Drawing Sheets

MODULE FOR CULTURING AND USING METABOLISMS AND/OR FOR MAINTAINING MICROORGANISMS

BACKGROUND OF THE INVENTION

The invention relates to a module for culturing and using metabolisms and/or for maintaining microorganisms, particularly cells or bacteria, as well as to a process for operating the module and the use thereof.

DESCRIPTION OF THE PRIOR ART

Material exchange apparatus, e.g. bioreactors, cell perfusion means or in general modules are known particularly in the field of liver support systems, and as an alternative method for animal tests or for producing biological cell products.

DE-CS 38 37 226 describes a perfusion apparatus for culturing and obtaining hepatocytes. This perfusion apparatus is characterized in that it contains a chamber with a cell compartment and a perfusion compartment, which are separated by a semipermeable membrane. The hepatocytes are immobilized in the hepatocyte compartment. Additional hollow fiber membranes in the cell compartment contain bile.

U.S. Pat. No. 3,734,351 describes a method for the liver-specific treatment of blood and a corresponding apparatus. The apparatus includes a chamber with three independent, superimposed compartments formed by two flat membrane inserts in the chamber. The first compartment contains blood, whose constituents can pass through the first membrane layer into the second compartment. The second compartment contains liver cells which metabolize the blood constituents. A second membrane subdivides the second compartment from the third compartment, which contains a dialyzate fluid. Into the third compartment materials are diffused from the cell or second compartment, which can be conveyed out of the same.

The material exchange between the cells and the blood or medium compartment is obtained in the prior art by diffusion. However, this has a disadvantageous effect on the cell metabolism and its controllability. As a result of the design resulting from the fact that the medium flows in on one side and, after diffusion through the membranes, passes out again, there is a different contribution for the cell substrate exchange between the medium inflow and outflow. In the initial area an increased substrate exchange occurs, but this decreases as the medium flows out through the hollow fiber membranes. Thus, the cells are exposed to a different contribution with respect to the substrate and metabolite exchange. Consequently there is no uniform substrate exchange and e.g. the metabolism of the cells and the viability thereof is significantly impaired.

French patent 2 660 323 also discloses a cell culturing module, which contains three independent membrane systems, which are once again spaced in such a way that there are significant material gradients with respect to the supply and disposal.

SUMMARY OF THE INVENTION

The problem of the present invention is to provide a module for material exchange between microorganisms, particularly cells, and a medium making it possible to improve the substrate and metabolite exchange and the metabolite exchange controllability and e.g. improve the metabolism and viability of the cells.

This problem is solved by a module and associated process in accordance with the present invention.

According to the invention the term module is understood to mean a material exchange apparatus in the form of a three-dimensional body, which includes an outer casing and an inner space the interior of the module housing a close packed space network. The module shape can vary widely. The module can e.g. have a rectangular or n-angular layout. Spherical or disk-shaped modules are also suitable for the purposes of the invention.

It is essential to the invention that use is made of at least three independent membrane systems, at least two independent membrane systems being constructed as hollow fiber membrane systems and the latter form in the inner area a close packed network.

A first independent hollow fiber membrane system is used for the medium inflow. A second independent hollow fiber membrane is provided for the supply of microorganisms, e.g. with oxygen, or removal of $CO_2$. The medium outflow is ensured by a third independent membrane system.

Each of the individual independent hollow fiber membrane systems comprises a plurality of individual hollow fiber membranes and in each case the hollow fibers of a system communicate with at least one inlet or an inlet and an outlet. This ensures that the hollow fibers of any particular independent system can be simultaneously supplied via the inlet, e.g. with medium.

In the inner space of the module the independent hollow fiber membrane systems form a three-dimensionally, close packed network in such a way that at virtually any point of the network a few microorganisms have virtually identical conditions for substrate supply. This leads to a substantial simulation of the conditions in the physiological organs with their own arteries and veins, such as e.g. the liver, with the arrangement of hepatocytes in lobuli. As a result of the independent arrangement of the different membrane systems the module offers the advantage of a decentral transport of nutrients, synthesis products and gases to and from a plurality of microorganisms independently of the position thereof in the module, as is the case in the cell environment in natural organs.

According to the invention the medium outflow is ensured by the third independent membrane system. This membrane system can also be a hollow fiber membrane or a changeable flat membrane or a changeable capillary membrane. What is decisive is that the third membrane system is also independent of the two other hollow fiber membrane systems.

A preferred embodiment proposes that the close packed network in the inner area is formed by three independent hollow fiber membrane systems. In this case all the independent membrane systems are hollow fiber membranes located in the inner area. The first independent hollow fiber membrane system is used for medium inflow, the second for medium outflow and the third for additional supply, e.g. with oxygen. The close packed network then comprises these three independent systems.

The close packed network can have different constructions, provided that it is ensured that in each case few microorganisms in the inner area have an identical substrate supply. The spatially close packed network can e.g. comprise close packed layers, in each case independent system layers alternating. A first layer comprising individual hollow fiber membranes is positioned horizontally. The second layer once again comprising individual hollow fiber membranes is positioned in the same plane, but rotated with respect to the first layer, e.g. at an angle of 90°. These layers alternate and together form a close packing system. The third independent hollow fiber membrane system, which once again comprises individual layers of hollow fiber membranes, traverses the said two layers, e.g. vertically from top to bottom and consequently "interweaves" the first two independent layers.

According to a further development of the invention, three independent hollow fiber membrane systems are so superimposed in alternating layer form, that all are positioned in one plane, but are in each case rotated by e.g. 60°.

This close packed network is placed in the inner area of the module. Due to the fact that each independent system communicates with at least one inlet or an inlet and outlet, it is ensured that the medium supplied reaches all locations in the module in a uniform manner and in the same way a uniform oxygen supply is obtained. Due to the third independent system for the medium outflow, continuously and uniformly the medium can be removed from all points of the entire module.

According to a preferred embodiment, in addition to the three hollow fiber membrane systems in the inner space, use is made of a further independent membrane system for the medium outflow. For this purpose, according to the invention either a replaceable flat membrane or a replaceable capillary membrane is fitted on the outer casing. This ensures that there is a problem-free medium outflow, even over long periods of time.

According to another development of the invention, the close packed network is formed by two independent hollow fiber membrane systems, a first being used for the medium inflow and a second for oxygen supply and the third independent membrane system is constituted by a replaceable flat or capillary membrane, which is fixed to the outer casing and is used for the medium outflow. The close packed network in the inner area and which is formed by the two hollow fiber membrane systems is constructed in the same way as described hereinbefore.

According to the invention, as hollow fiber membranes preference is given to the use polypropylene, polyamide, polysulphone, cellulose or silicone. The choice of the hollow fiber membranes is a function of the molecules provided for the material exchange. However, according to the invention, it is possible to use all standard hollow fiber membranes, which are known from the prior art for material exchange apparatuses.

According to the invention, when using three independent hollow fiber membrane systems, which in the inner area form a close packed network, a capillary system of liquid-impermeable capillaries, such as e.g. of refined steel or glass can be used. This can then be used for the thermostatic control of the module with its inner area. It also permits a uniform cooling of the module with its inner space and introduced microorganisms to below −20° C. According to a further development of the invention, it is also possible to use further hollow fiber systems for thermostatic control or for cooling to below the freezing point.

A further preferred development proposes that the outer casing is formed by a sealing compound in which the capillaries are cast. The outer casing cast in such manner that there is an access from the outside into the volume of the capillaries.

According to a further development the module has different accesses which provide access to the module. A first access into the internal area of the module serves for introducing the microorganisms into the module, whilst other accesses are used for the pressure, pH and temperature measurements within the inner area of the module.

The invention also relates to a process for operating the module. According to the invention the inner area of the module is filled with microorganisms. Following on to this the physiological conditions necessary for culturing and/or obtaining are set. The medium is fed into a first independent hollow fiber membrane system, passes through the hollow fiber membrane and metabolizes with the microorganisms, which are either located in the cavities or adhere to the membranes. The material exchange between the microorganisms and the medium takes place by convection. In order to ensure this, it is merely necessary for the outlet on the independent hollow fiber membrane system into which the medium is supplied to be closed, so that the medium must pass through the hollow fiber membranes. However, the module according to the invention can also be operated in the diffusion operating mode, in that the outlet for the medium flow in the independent hollow fiber membrane system is left open and consequently there is only a diffusion operation. The particular advantage of the invention is that as a result of convection operation there is an optimum, controllable substrate exchange, whereas in the prior art there is only a material exchange by diffusion.

The invention offers the further advantage that the hollow fiber membranes or capillaries can be coated with a substrate suitable for the cells or microorganisms in order to provide microorganism adhesion to the capillary systems.

A further advantage of the invention is that in addition to the cell type used, one or more other cell types can be used in accordance with a coculture procedure. These additional cell types can be cultured in the lumen of one or more independent capillary systems. Cells for coculturing are e.g. non-parenchymal cells from liver sinusoids.

The module according to the invention offers to the further advantage that one of the independent membrane systems can be used for conveying away e.g. bile constituents.

According to a further advantageous variant, one of the independent membrane systems is used for dialysis.

As a result of the proposed independent membrane systems, there is a considerable scope for very varied uses of the module.

According to a particularly preferred embodiment the microorganisms are cells and in particular liver cells.

BRIEF DESCRIPTION OF THE DRAWINGS

The invention is described in greater detail hereinafter relative to non-limitative embodiments and the attached drawings, wherein.

DETAILED DESCRIPTION OF THE PREFERRED EMBODIMENT OF THE INVENTION

Figure 1:
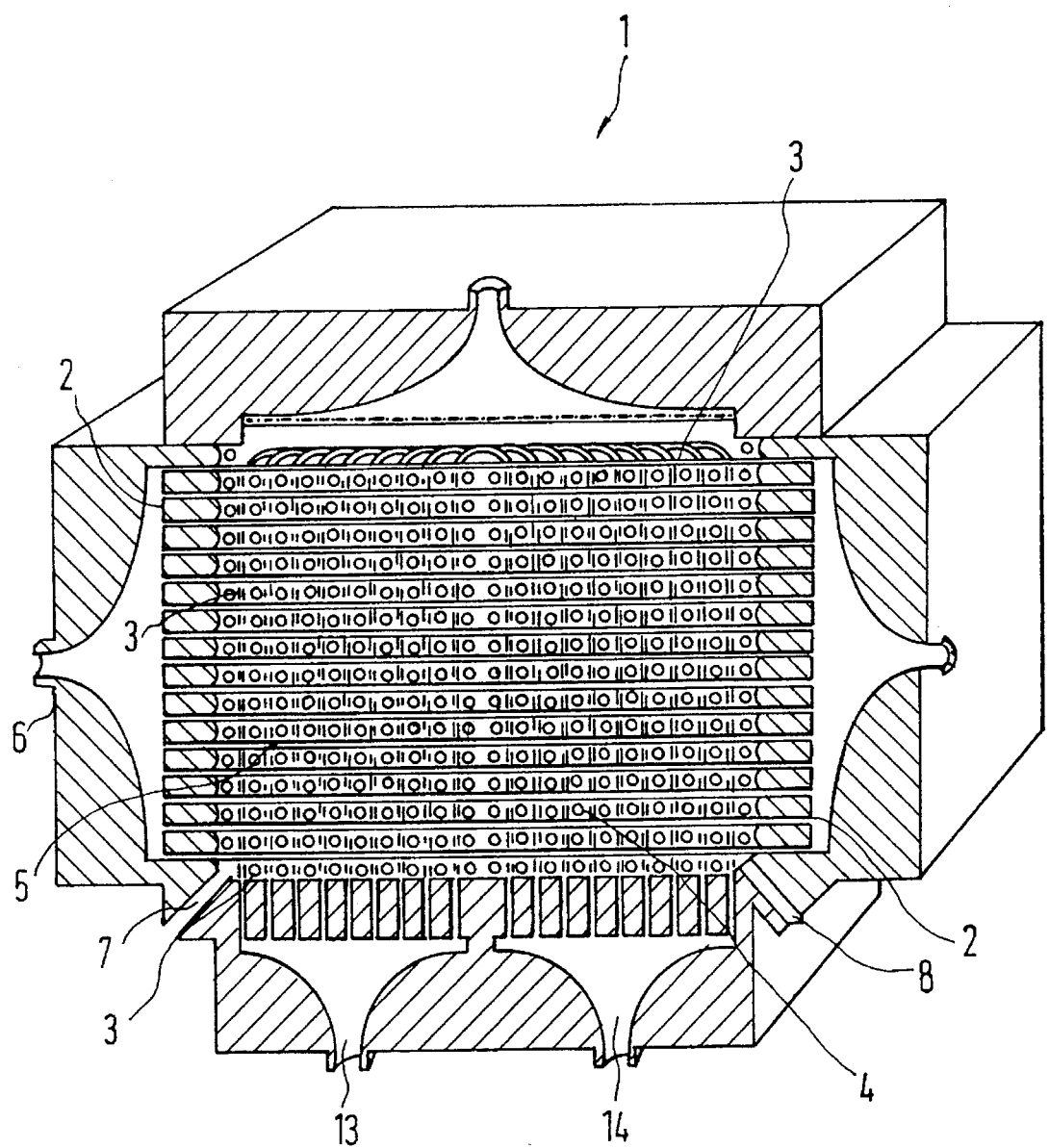
FIG. 1 is a cross-section through a module having a rectangular shape.

FIG. 1 is a vertical cross-section through a possible module design showing a module 1 having a close packed network 5 of three independent systems. The module 1 includes an outer casing 2 and an inner space 4 housing the close packed network 5. The outer casing 2 comprises a sealing compound in which the capillaries are cast. The outer casing 2 has an access from the outside into the internal diameter of the capillaries. The sealing compound maintains the mechanical stability of the module. The close packed network 5 in the inner space 4 of the module 1 has the following construction.

A first independent hollow fiber membrane system is formed by layers of hollow fibers 3, the first layers being positioned horizontally. Each individual layer comprises linear hollow fiber membranes 3, which are closely juxtaposed. The second independent hollow fiber membrane system is also formed by layers, which are turned by an angle of 90° in the same plane, so that layers of the two independent systems alternate. These layers are in part represented by circles in FIG. 1. These alternating layers are now tightly superimposed in a module 1. In a test module with external dimensions 12×12 cm approximately 100 layers are superimposed. The third independent hollow fiber membrane system is represented by vertical lines in FIG. 1. These lines represent hollow fiber membranes, which vertically traverse from top to bottom the layers located in a single plane. In the described test module there are approximately 50 layers, which interweave the module vertically from top to bottom. As a result of this design of the close packed network it is ensured that few cells, as can be seen FIGS. 2a and 2b, have an identical substrate supply.

For the operation of the module medium is supplied through the medium inflow head 6 into the internal diameter of the capillaries. The end opposite to the head 6 is closed. This medium now passes through the membranes of the capillaries and there is a material exchange with the cells 9, which are either located in the cavities and/or adhere to the capillaries. The cells 9 are supplied with oxygen during the material exchange. The oxygen passes through the oxygen inflow head 13 into the internal diameter of the capillaries and is removed via the oxygen outflow head 14. In the present case the hollow fiber membranes 3 of the independent system for the oxygen supply are formed by U-shaped hollow fiber membranes. The conveying away of the material takes place via the third independent hollow fiber membrane system through the membranes indicated by the circles. These hollow fiber membranes then issue into a medium outflow head 15, from where the medium can be removed (not shown).

Cells 9 can be supplied through the access 7 into the inner area of the module 1. A further access 8 is provided for carrying out measurements in the inner area of the module, such as e.g. pressure, temperature or pH measurements.

The described module construction can be varied at random. The module shape need not be rectangular and can instead equally well be n-angular or some other random hollow body, provided that the hollow body makes it possible to house in an inner space 4 a close packed network 5 of independent hollow fiber membrane systems. What is essential to the invention is the design of the close packed network 5 of the hollow fiber membrane system. Diverging from the possibilities shown in FIG. 1 it is equally possible to superimpose in close packed manner individual layers, each individual layer being formed from alternating, independent hollow fiber membranes. According to another possibility the first two layers are at an angle α of 0 to 180°, instead of 90°. Random possibilities also exist for the third independent hollow fiber membrane system, provided that it is ensured that there is an almost identical substrate supply both for the medium supply, the oxygen supply and the medium outflow.

Figure 2A:
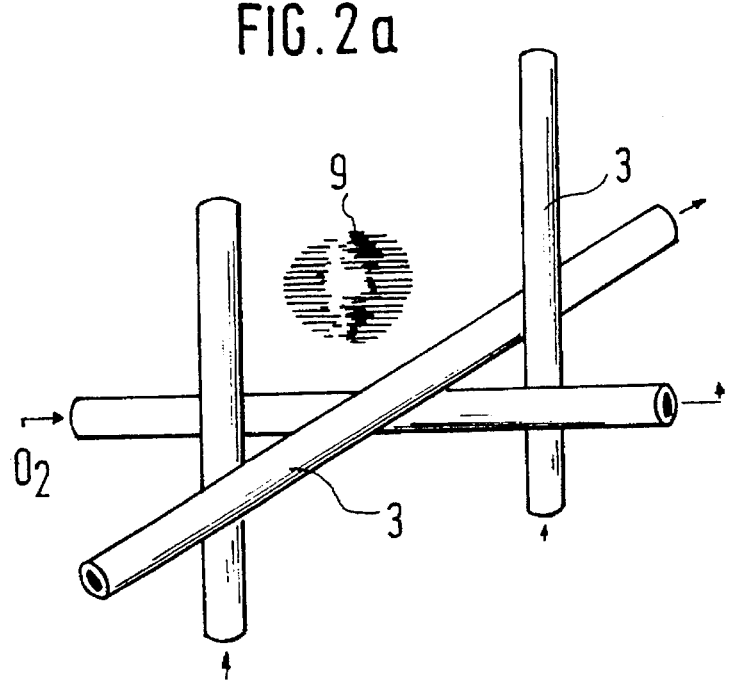
FIG. 2 shows individual hollow fiber membranes, corresponding to FIG. 1, of three independent membrane systems.
Figure 2B:
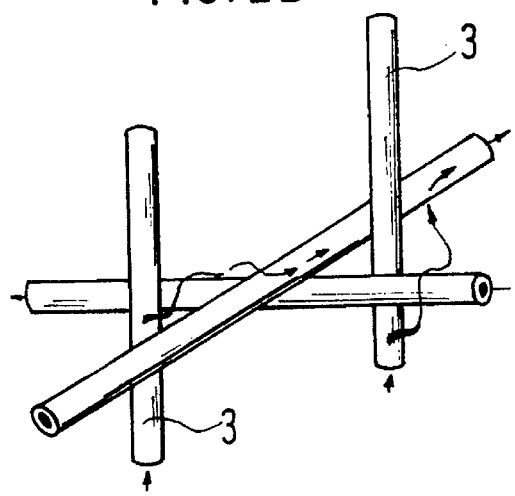
Figure 3A:
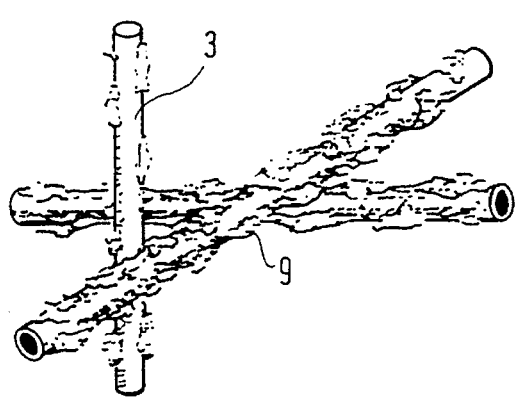
FIGS. 3A, 3B, 3C, 3D, and 3E show: independent hollow fiber membrane systems according to FIG. 1 with cell cultures.
Figure 3B:
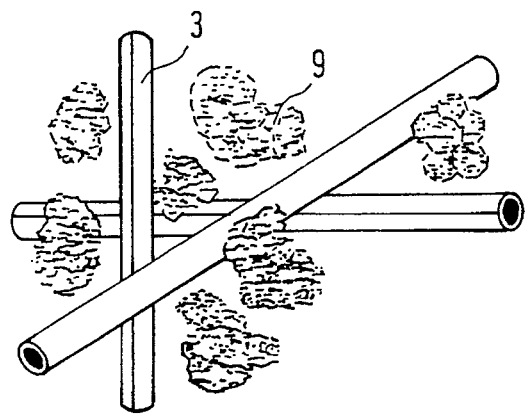
Figure 3C:
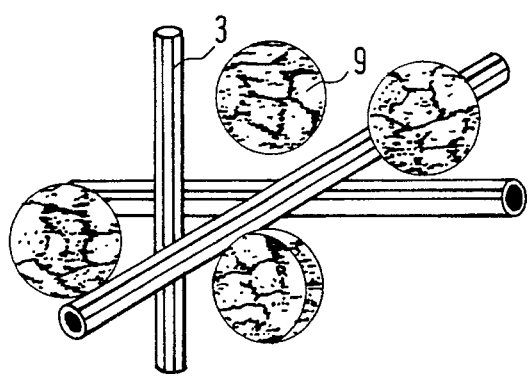
Figure 3D:
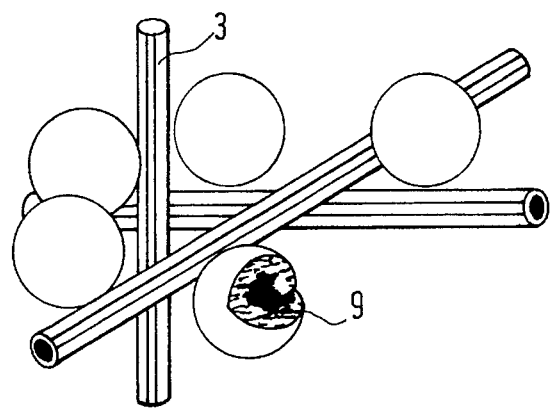
Figure 3E:
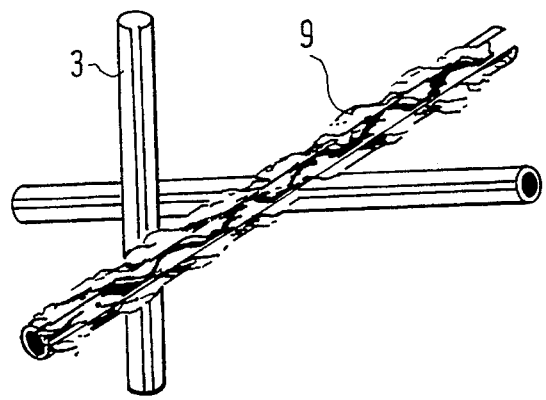

FIG. 2 shows individual hollow fibers 3 of three independent hollow fiber membrane systems. FIGS. 3A and B show a random point from the inner space 4 of the module 1. FIGS. 2a and b reveal the essential concept of the invention. As indicated by the arrows, medium is supplied through the hollow fiber membrane 3, which is a single membrane from a first independent membrane system, said medium passing through the membrane 3. The microorganisms 9, here in the form of cells, are located in the cavities of the close packed network 5 and/or, as shown in FIG. 3, adhere to the capillaries. A material exchange takes place between the cells 9 and the medium. According to the invention, through a further independent hollow fiber membrane system, a single membrane 3 being shown in FIGS. 2a and 2b, the cells are e.g. supplied with oxygen (horizontal membranes). A third independent hollow fiber membrane system, once again only represented by an individual membrane 3, is used for the medium outflow. Thus, the medium is removed after exchange with the cells.

The individual hollow fiber membranes shown in FIGS. 2a and 2b are components of the close packed network 5 in the interior of the module 1 and which is constructed in such a way (FIGS. 1 and 10), that at each point within the module 1, there are identical substrate supply conditions. At each point of the module 1 the cells 9 are uniformly supplied and consequently an optimum material exchange and controllability thereof are ensured. FIG. 2b shows the perfusion of the cells 9 and the medium flow along the capillaries. As a result of the design according to the invention the situation is very similar to the true conditions, e.g. in the liver.

FIG. 3 shows different cell culture methods within the module. According to the invention the microorganisms 9 can be placed in different ways in the module 1. FIG. 3A shows an adhesion culture to the membranes, FIG. 3B an aggregate culture between the membranes, FIG. 3C microcarrier cultures between the membranes, FIG. 3D capsule cultures between the membranes and FIG. 3E cocultures in separate membrane compartments. As a result of the inventive construction of the module 1, i.e. through the close packed network in the inner area of the module constituted by individual hollow fiber membranes, it is possible to use different cell culture methods and therefore achieve a greater scope of use for the invention.

Figure 4:
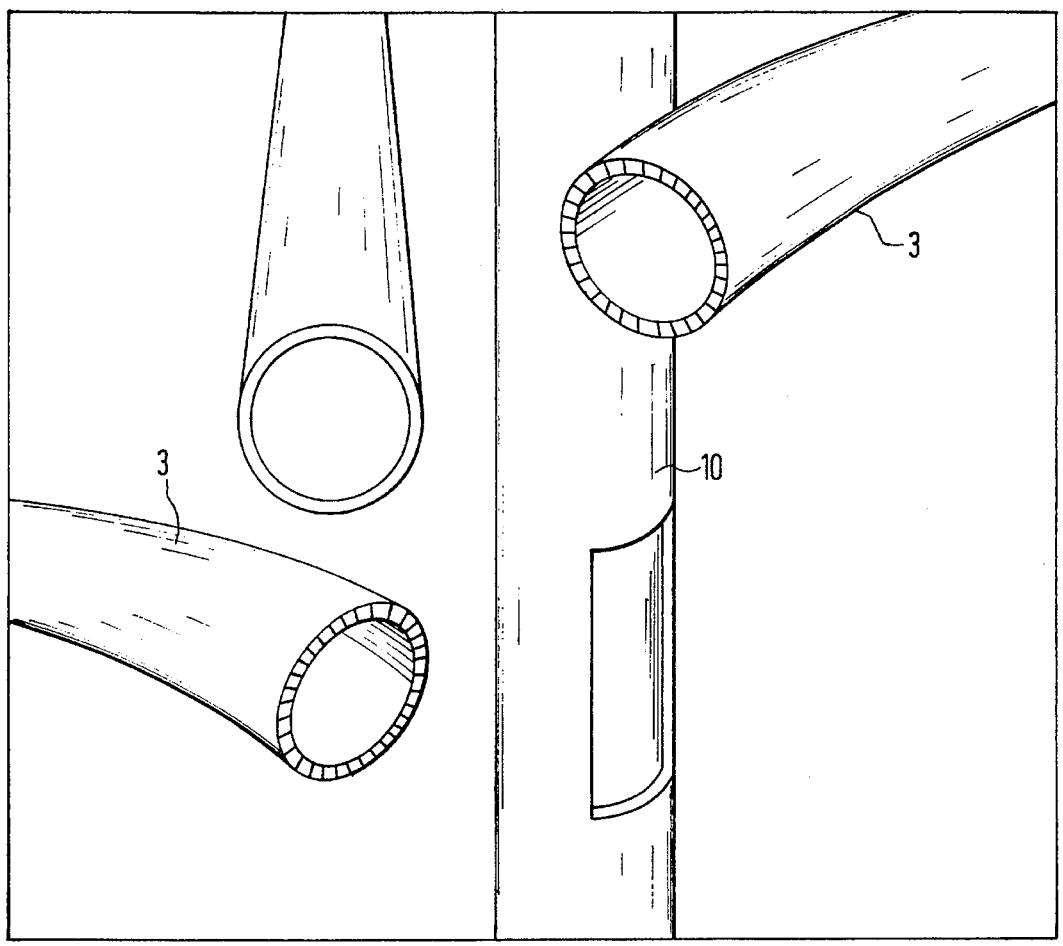
FIG. 4 shows individual capillaries of four independent systems.

FIG. 4 shows individual capillaries of four independent systems and how the capillaries are coated with adhesion factors. There are three systems in one plane. FIG. 4 shows four independent membrane systems, which are in each case part of an overall system. As described relative to FIGS. 1 and 2, one hollow fiber membrane system 3 is used for medium inflow, a third system for oxygenation and a further independent system 10 e.g. for dialysis, as a heat exchanger for the lyophilization of cells or for cocultures with further cell types. The black points on the membranes 3 indicate the pore openings (cells not shown). Through the provision of four different independent hollow fiber systems, it is possible to significantly broaden the possible uses of the object of the invention. Apart from the essential advantage of the invention that there is an identical substrate supply for virtually any cell within the module, the invention also makes it possible by coating the capillaries with adhesion factors within the module to house a maximum number of cells, which are virtually all subject to the same substrate supply and therefore have an increased life.

Figure 5:
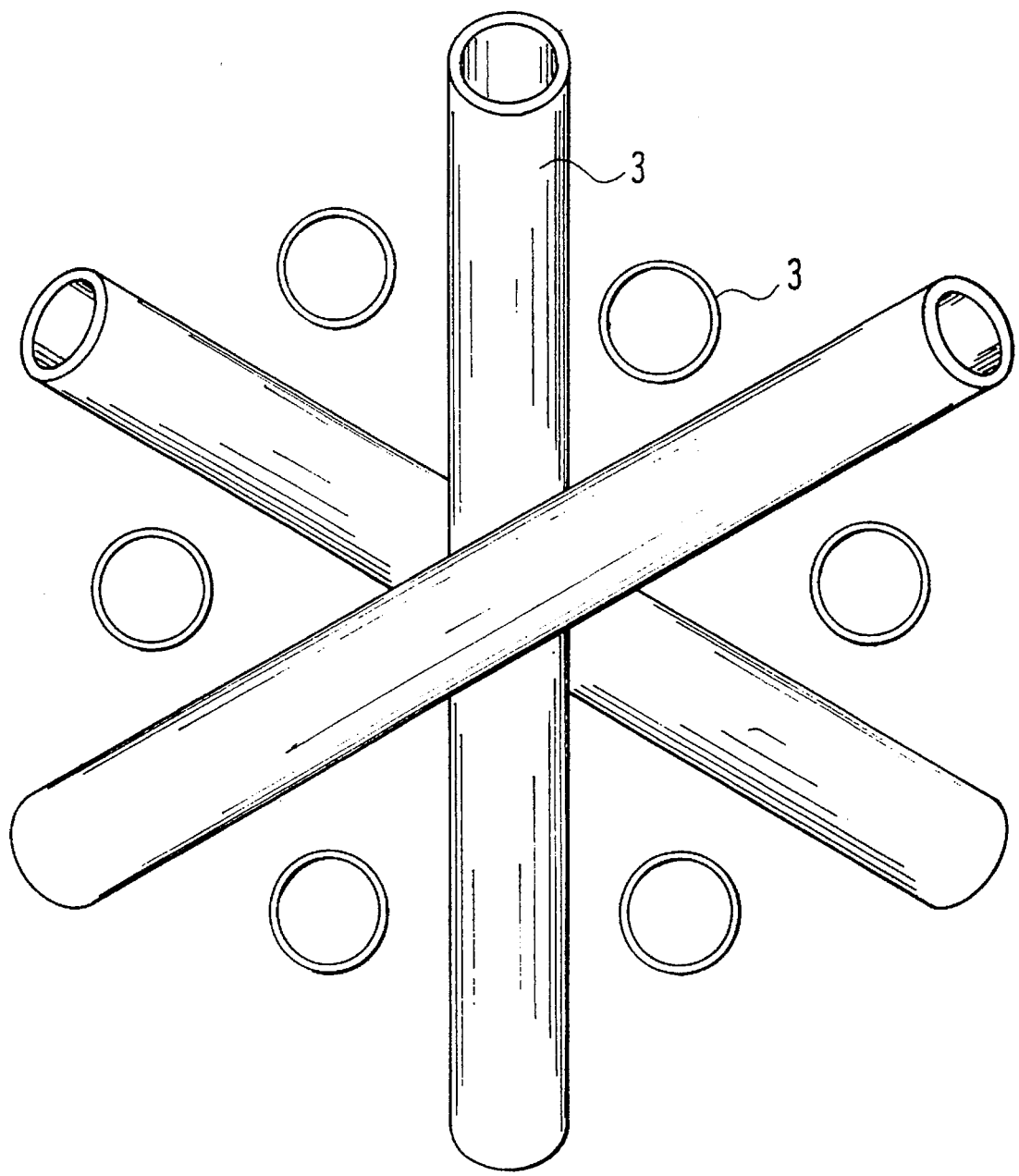
FIG. 5 is a perspective view of a plane of a module with four independent hollow fiber membrane systems according to FIG. 4.

FIG. 5 shows in a three-dimensional plan view a plane of a module with four independent hollow fiber systems like FIG. 4. A first independent system is used for the medium inflow, a second for medium outflow and a third for oxygen supply. A fourth independent hollow fiber system can be used for dialysis or as a heat exchanger for the lyophilization of the cells or for cocultures.

Figure 6:
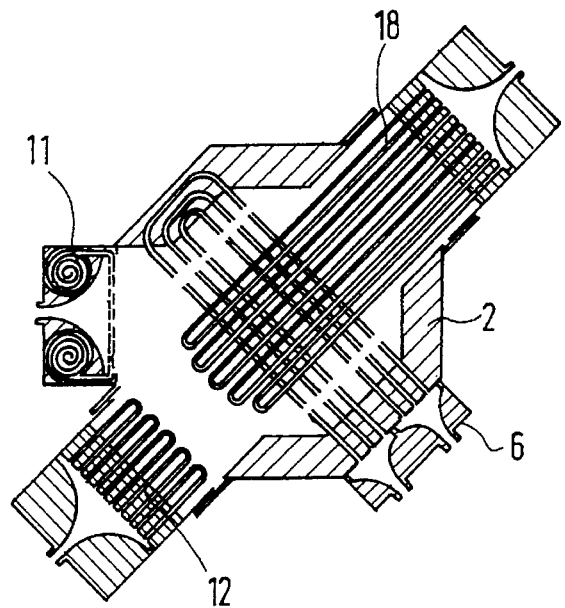
FIG. 6 illustrates three possibilities of medium outflow from a module.

FIG. 6 shows different possibilities of the medium outflow from the module 1. In the inventive constructions described relative to FIGS. 1 to 5 the medium outflow has taken place by means of the hollow fiber membranes 3. According to a further development the medium outflow not only takes place through hollow fiber membranes, which are a component of an independent hollow fiber system within the close packed network 5, but also through a number of variants. FIG. 6 shows the different possibilities. The outflow either takes place by means of fixed inserted capillary membranes (connected to the outlet head 6) spatially and in a predetermined arrangement with respect to the remaining capillary membranes, or via replaceable capillary membranes 12, which are also spatially independent with respect to the remaining membrane systems. The replaceable capillary membrane 12 is fixed to the outer casing 2, which must have an opening suitable for receiving said membrane 12.

According to another variant replaceable flat membranes 11 are located on the outer casing 2, which must contain corresponding openings. According to a further variant use is made of replaceable capillary membranes 18, which can be drawn out in the case of blockages.

It is decisive that the specific medium outflow devices are independent of the further hollow fiber membrane system. These different medium outflow devices can be supplied in addition to an already present medium outflow via a hollow fiber capillary membrane forming part of the close packed network.

Figure 7:
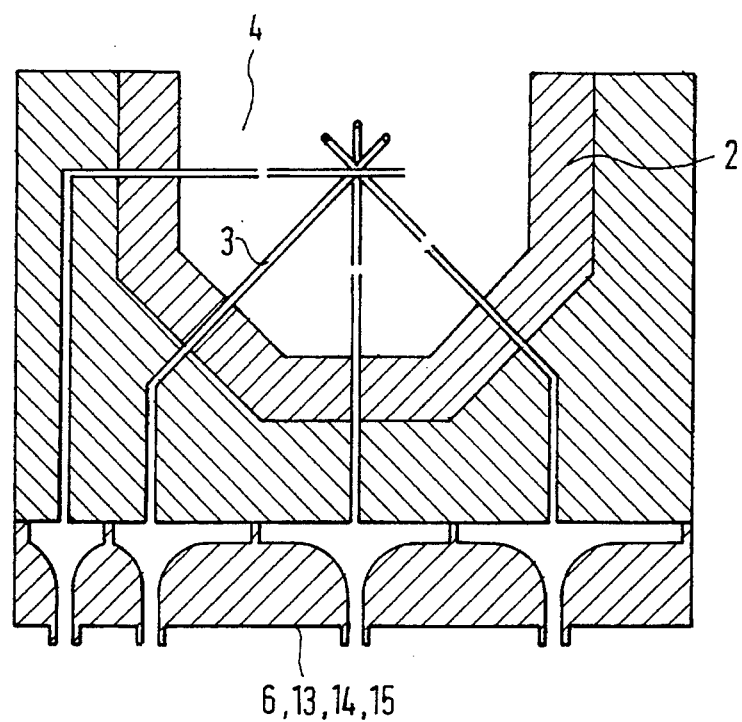
FIG. 7 illustrates alternative arrangements of the membrane heads on one side of a module.

FIG. 7 shows a special arrangement of membrane heads 6, 13, 14, 15 on one side of the module 1. This design of the invention, i.e. the arrangement of all the inflows and outflows on the outer faces of the module 1 on a single side offers the advantage that all the connections are in one plane.

Figure 8:
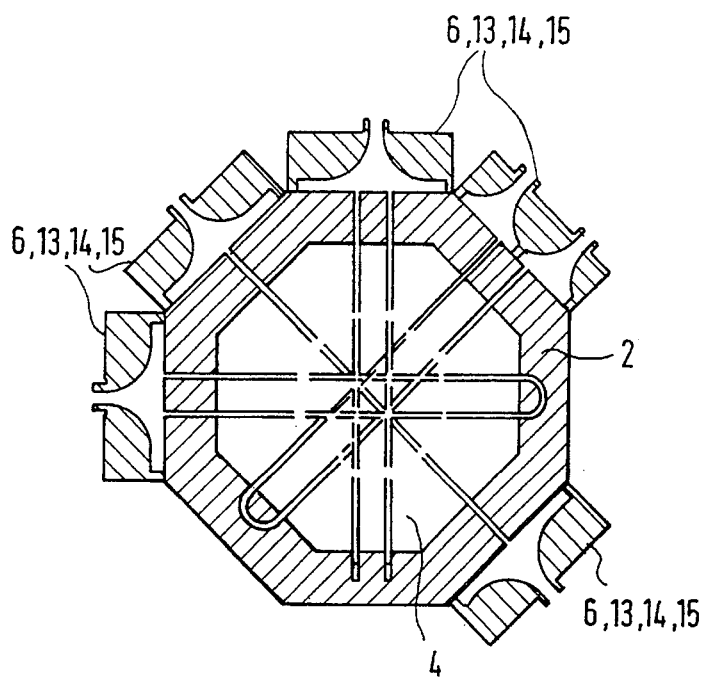
FIG. 8 is a sectional view through a module with hollow fiber membranes and membrane heads with different types of hollow fiber membranes.

FIG. 8 is a cross-section of an octagonal module with capillary membranes and membrane heads 6, 13, 14, 15. FIG. 8 once again shows the different possibilities as to how the capillaries can be located in one plane. Thus, the capillaries can be in double-tube form with one head for the medium inflow and outflow. According to another variant one capillary is straight and has a corresponding head for the medium inflow. According to a third possibility there is a single straight capillary with a dead end and a head for medium inflow and outflow. In a fourth possibility there is a double-tube capillary with circulation and a head for medium inflow and outflow.

Figure 9:
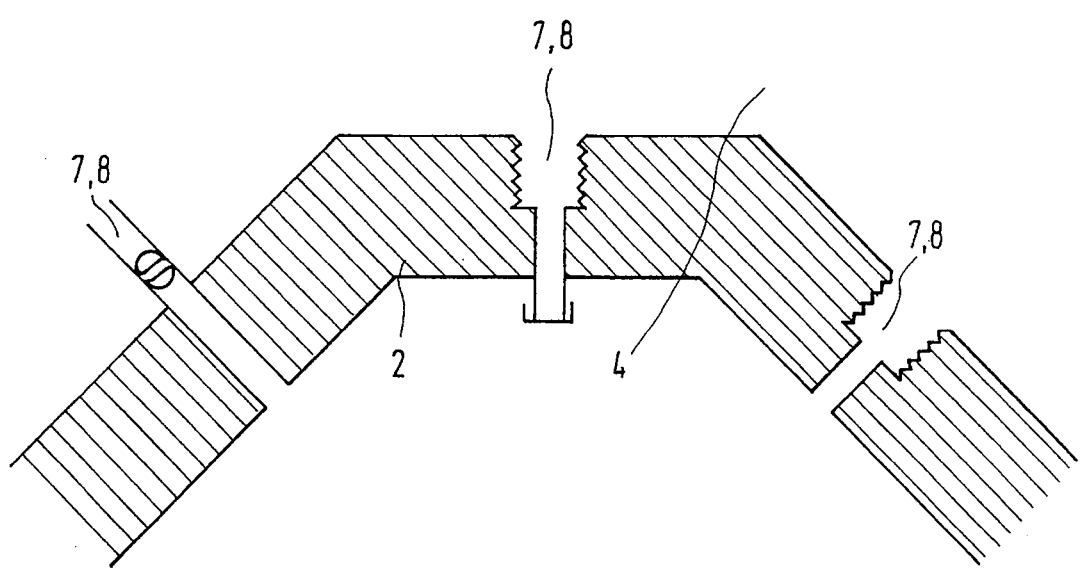
FIG. 9 is a fragmentary sectional view showing different accesses to the module.

FIG. 9 shows the different accesses in the module casing which provide access to the module inner space 4. Thus, the module can have different accesses 7, 8, in order to carry out measurements for the pressure, temperature, flow, pH or osmolarity.

Figure 10:
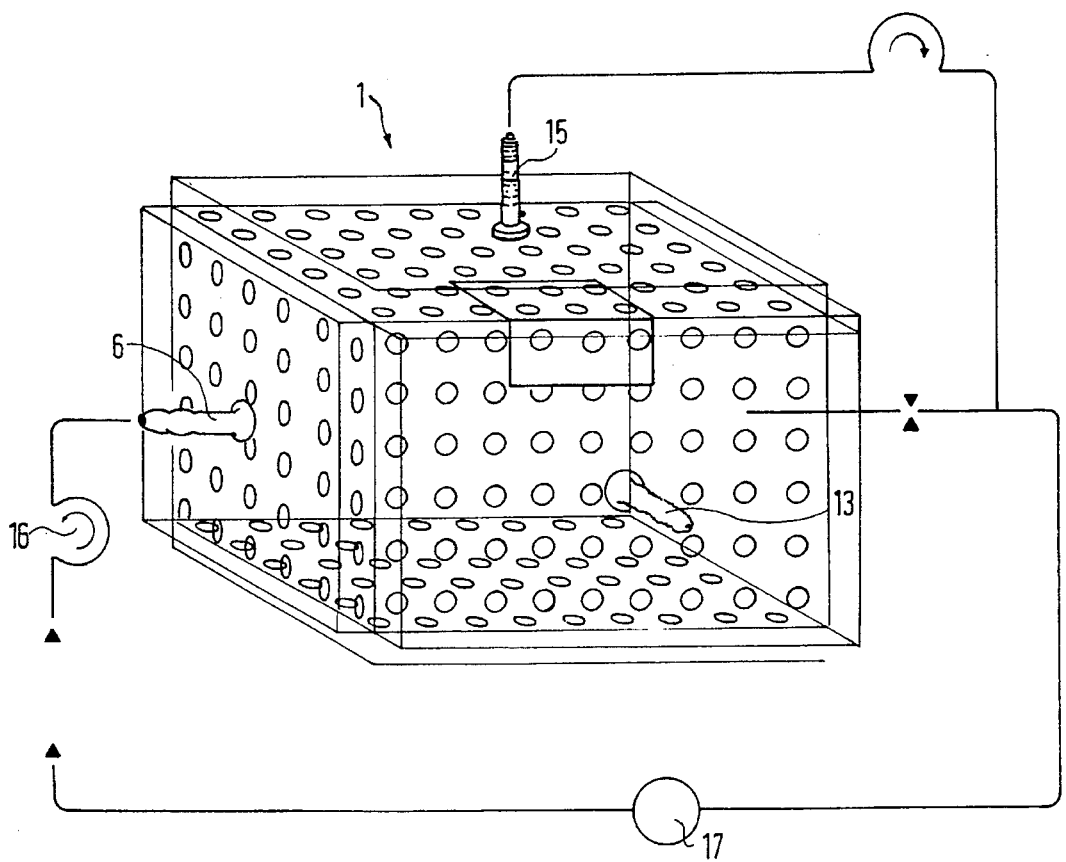
FIG. 10 is a schematic view illustrating an exemplified use of a module as an extracorporeal support system.

FIG. 10 shows the use of a module 1 as an extracorporeal liver support system. The medium, in this case the blood plasma, is supplied via a blood pump 16 into the medium inflow head 6 of the module. Oxygen supply takes place by means of the inflow head 13. The oxygen is removed again via the outflow head 14 (not shown). The medium removal takes place by means of the medium outflow head 15 and corresponding control and pump units 17.

As a result of the design according to the invention, all the cells in the system have the similar substrate supply conditions. The medium to be supplied is uniformly provided at all locations within the module, as is the oxygen supply. Through the use of different capillaries a selective removal, e.g. lipophilic substrates is possible. As a result of the design according to the invention the life of e.g. liver cells could be increased from 10 days to 7 weeks and the activity increased by 40%.

What is claimed is:

1. A module for culturing microorganisms under generally identical medium supply and disposal conditions, said module comprising:

(a) an outer casing defining an enclosed inner space for retaining microorganisms, said outer casing including a plurality of capillaries formed in said outer casing;

(b) at least one access aperture formed in said outer casing to provide access to the inner space for introducing microorganisms into the inner space; and (c) a close packed network positioned in the inner space of said outer casing, said close packed network including a first independent hollow fiber membrane system having an open inlet and closed outlet for inflow and convection of a medium into the inner space, a second independent hollow fiber membrane system having an inlet for inflow of oxygen into the inner space, and a third independent hollow fiber membrane system for having an outlet for outflow of the medium from the inner space, the first, second, and third membrane systems being intersected and superimposed in a three dimensional array such that the microorganisms in the inner space have generally identical medium supply and disposal conditions.

2. A module according to claim 1, wherein, said first, second, and third membrane systems in the close packed network are hollow fiber membranes selected from the group consisting of polypropylene, polyamide, polysulphone, cellulose, or silicone.

3. A module according to claim 1, further comprising, an additional independent membrane system, said additional membrane system being a replaceable flat membrane fitted onto said outer casing to ensure medium outflow over time.

4. A module according to claim 1, further comprising, an additional independent membrane system, said additional membrane being a replaceable capillary membrane on said outer casing to ensure medium outflow over time.

5. A module according to claim 1, further comprising a fluid-impermeable, independent capillary system inside the inner space.

6. A module according to claim 1, wherein said close packed network includes a plurality of cavities, the microorganisms being retained in the cavities or adhered to the membranes.

7. A module according to claim 1, wherein said outer casing is formed by a sealing compound with cast capillaries, said capillaries providing access from the outside of the outer casing through the internal diameter of the capillaries into the inner space.

8. A module according to claim 1, wherein the capillaries in said outer casing include inlet and outlet heads to facilitate and control the communication of medium with the independent capillary system of said close packed network.

9. A module according to claim 1, wherein said outer casing includes an access extending through said outer casing into said inner space in order to introduce the microorganisms into the module and to obtain pressure, temperature, or pH measurements.

10. A module according to claim 1, wherein perforated tube extends into the module through an access to facilitate a uniform distribution of the microorganisms in said inner space.

* * * * *